United States Patent [19]

Doane

[11] Patent Number: 4,724,056
[45] Date of Patent: Feb. 9, 1988

[54] POLLUTION-FREE PROCESS FOR MAKING TRIALKYL PHOSPHITES

[75] Inventor: Elliott P. Doane, Monroe, Conn.

[73] Assignee: Stauffer Chemical Company, Westport, Conn.

[21] Appl. No.: 21,935

[22] Filed: Mar. 5, 1987

[51] Int. Cl.⁴ .................... C25B 1/00; C25B 3/00
[52] U.S. Cl. .................... 204/72; 204/59 R; 204/131; 558/96
[58] Field of Search ............... 558/96; 204/59 R, 72, 204/131

[56] References Cited

U.S. PATENT DOCUMENTS

| 4,337,125 | 6/1982 | Kuck et al. | 204/72 |
| 4,394,226 | 7/1983 | Wade | 204/72 |
| 4,572,769 | 2/1986 | Shimizu | 204/72 |

OTHER PUBLICATIONS

Baizer, Organic Electrochemistry, Marcel Dekker Inc., N.Y., N.Y., 1973, pp. 510–512.
Weinberg, Technique of Electrorganic Synthesis, John Wiley & Sons, N.Y., N.Y., 1904, pp. 565–574.

Primary Examiner—Arthur P. Demers
Attorney, Agent, or Firm—Richard P. Fennelly

[57] ABSTRACT

A pollution-free process for forming trialkyl phosphite by reaction of phosphorus trichloride with alcohol in the presence of a tertiary amine acid acceptor is described in which by-product hydrochloride salt of the acid acceptor is electrolyzed to regenerate the tertiary amine for recycle for further use in reacting additional phosphorus trichloride with alcohol to form additional trialkyl phosphite product.

7 Claims, 1 Drawing Figure

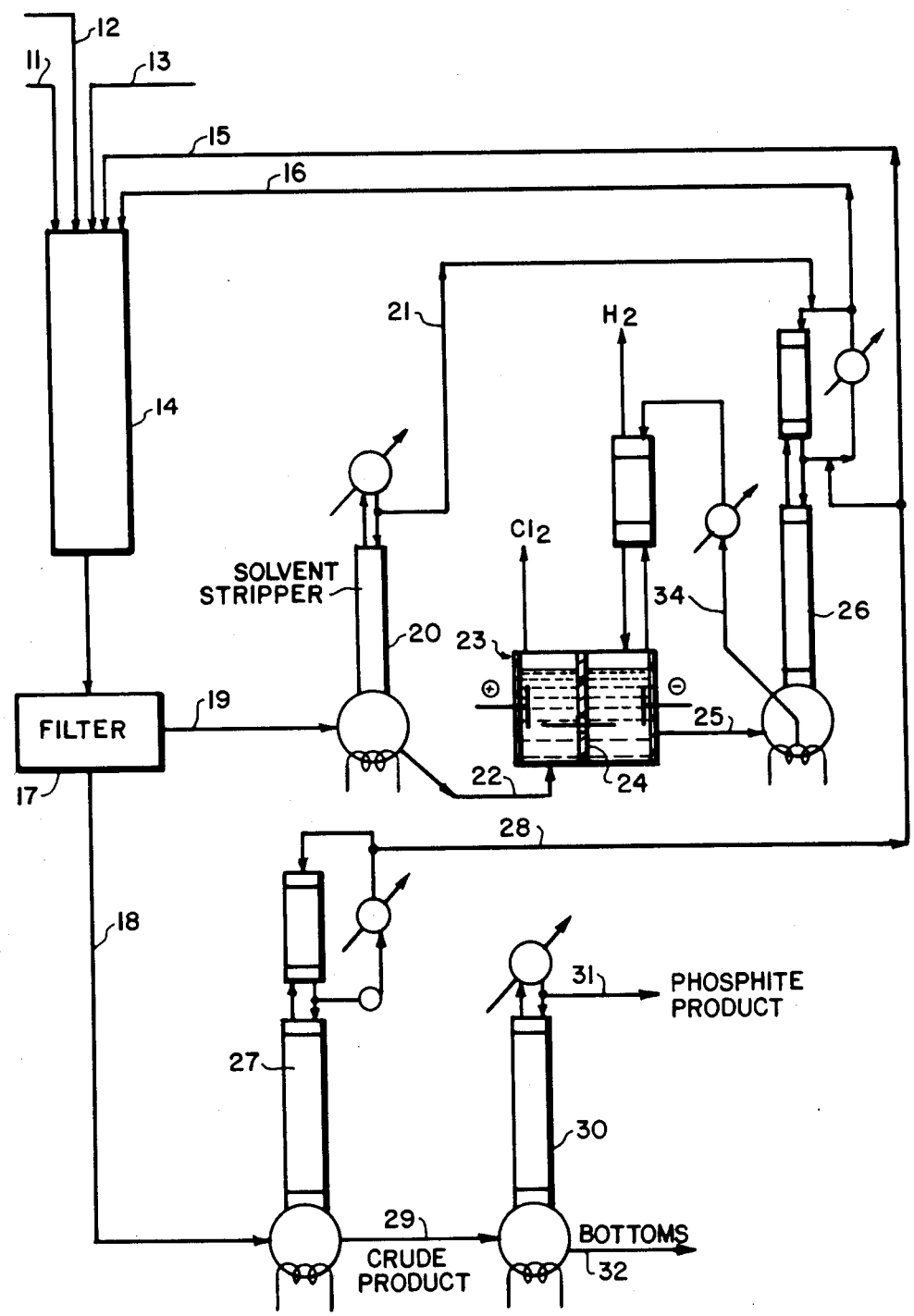

POLLUTION-FREE PROCESS FOR MAKING TRIALKYL PHOSPHITES

BACKGROUND OF THE PRESENT INVENTION

1. Field of the Present Invention

The present invention is a pollution-free process for making trialkyl phosphites by the reaction of phosphorus trichloride ($PCl_3$) with an alcohol in the presence of an amine acid acceptor.

2. Description of the Prior Art

The general reaction wherein $PCl_3$ is reacted with alcohol in the presence of an acid acceptor, such as ammonia or an amine, is well known. Processes of this type are used commercially. However, the use of an amine as the acid acceptor in such processes results in the formation of an amine hydrochloride salt which is an undesired by-product. The use of mono-, di-, or trialkyl amine acid acceptors, such as triethyl amine, in such a process results in a waste salt brine that raises disposal problems.

Therefore, a need exists in regard to the current known processes for a more pollution-free process wherein the hydrochloride salt of the amine acid acceptor is utilized in a manner which does not give rise to disposal problems.

SUMMARY OF THE PRESENT INVENTION

The process of the present invention is an improved process for forming a trialkyl phosphite by the reaction of phosphorus trichloride with alcohol in the presence of a tertiary amine acid acceptor. The process comprises the reaction of the trichloride and alcohol in the presence of acid acceptor and solvent to form a reaction mixture which contains the desired trialkyl phosphite product, solvent, and the hydrochloride salt of the amine acid acceptor as an undesired by-product. The process involves the subsequent step of electrolyzing the hydrochloride salt of the amine acid acceptor after it has been removed from the reaction mixture to regenerate the tertiary amine which can then be recycled for further use in reacting additional phosphorus trichloride with alcohol to form additional trialkyl phosphite.

DESCRIPTION OF THE DRAWING

The present invention will be further understood by reference to the Drawing which is a flow diagram showing a preferred embodiment of the process of the present invention.

DETAILED DESCRIPTION OF THE PRESENT INVENTION

The flow chart which constitutes the Drawing for the present process illustrates a preferred embodiment thereof. The reactants and amine acid acceptor are fed via lines 11-13 to a cooled reactor 14 along with additional recycle alcohol, amine acid acceptor and solvent (as will be described below) through lines 15 and 16. A representative feed ratio is 177 parts by weight amine (preferably trimethyl amine), 137.5 parts by weight of $PCl_3$ and 96.0 parts by weight of alcohol (e.g., methanol) combined with 270 parts by weight of recycle hexane. 9.6 parts by weight of methanol and 8.9 parts by weight of trimethyl amine. The reaction proceeds in reactor-cooler 14 in known manner yielding a reaction mixture principally comprising solvent, trialkyl phosphite product, unreacted alcohol, amine acid acceptor, and hydrochloride salt of the acceptor. A filter 17 removes solids (principally the crude hydrochloride salt of the amine acid acceptor) from the liquid reaction mixture yielding a filtrate in line 18 principally containing solvent, product, unreacted alcohol, and amine acid acceptor. The solid residue from the filter is washed with solvent and the hydrochloride salt of the amine acid acceptor is dissolved in water. The resulting mixture is passed through line 19 first to solvent stripper 20 which removes solvent overhead in line 21. The remaining aqueous solution containing the hydrochloride salt of the amine acid acceptor is sent via line 22 to an electrolysis unit 23 containing cation membrane 24. This unit 23 regenerates the amine acid acceptor which is fed via line 25 to a still 26 which feeds regenerated acid acceptor dissolved in solvent from the solvent stripper 20, via line 16 back to reactor 14. The electrolysis unit 23 also produces chlorine, which can be dried and reacted with elemental phosphorus to form $PCl_3$ for recycle to reactor 14, and hydrogen, which is both a valuable chemical and a clean burning fuel. A stream of liquid water 34 is withdrawn from the bottom of the still, cooled, and used to remove vaporized amine acid acceptor from the hydrogen.

The filtrate from filter 17 which is in line 18 is first fed to still 27 for recovery of solvent, unreacted alcohol and unused amine acid acceptor for eventual passage via line 28 to recycle line 15. The crude phosphite product will be sufficiently pure for many commercial purposes. However, if a purer grade phosphite product is desired, the crude phosphite product can be passed via line 29 to still 30 for recovery of purified phosphite product in line 31. The small bottoms stream 32 from still 30 can be fed to an incinerator (not shown) or disposed of by other means.

In preferred embodiments, hexane is the preferred solvent since it is relatively cheap and is non-toxic, stable and inert and has a convenient boiling point (68.7° C.) giving a good differential to that of trimethyl phosphite (111° C.), for example. A mixture of 6-carbon paraffinic isomers will be even less costly than n-hexane, and such a mixture will work equally well. Trimethyl amine is preferred over triethyl amine because its hydrochloride is deemed to be stable in the anode compartment of the membrane cell and it is cheaper.

The foregoing represents certain preferred embodiments of the present invention and therefore should not be construed in a limiting sense. The scope of protection that is sought is set forth in the claims which follow.

I claim:

1. A process for forming a trialkyl phosphite by reaction of phosphorus trichloride with alcohol in the presence of a tertiary amine acid acceptor which comprises:
   (a) reacting the trichloride and alcohol in the presence of the acid acceptor and solvent to form a reaction mixture which predominantly contains trialkyl phosphite product, solvent and the hydrochloride salt of the amine acid acceptor as a by-product; and
   (b) electrolyzing the hydrochloride salt of the amine acid acceptor after it has been removed from the reaction mixture to regenerate the tertiary amine acid acceptor which is recycled for further use in reacting additional phosphorus trichloride with alcohol to form additional trialkyl phosphite product.

2. A process as claimed in claim 1 wherein the trialkyl phosphite is trimethyl phosphite.

3. A process as claimed in claim 1 wherein the trialkyl phosphite is triethyl phosphite.

4. A process as claimed in claim 2 wherein the acid acceptor is trimethyl amine.

5. A process as claimed in claim 3 wherein the acid acceptor is trimethyl amine.

6. A process as claimed in claim 4 wherein the solvent is hexane.

7. A process as claimed in claim 5 wherein the solvent is hexane.

* * * * *